US006989167B2

(12) United States Patent
Howie et al.

(10) Patent No.: US 6,989,167 B2
(45) Date of Patent: Jan. 24, 2006

(54) METHOD FOR REDUCING ACRYLAMIDE IN FOODS COMPRISING REDUCING THE LEVEL OF REDUCING SUGARS, FOODS HAVING REDUCED LEVELS OF ACRYLAMIDE, AND ARTICLE OF COMMERCE

(75) Inventors: John Keeney Howie, Oregonia, OH (US); Peter Yau Tak Lin, Liberty Township, OH (US); David Vincent Zyzak, Mason, OH (US); Richard Gerald Schafermeyer, Cincinnati, OH (US)

(73) Assignee: Procter + Gamble Co., Cincinnati, OH (US)

( * ) Notice: Subject to any disclaimer, the term of this patent is extended or adjusted under 35 U.S.C. 154(b) by 68 days.

(21) Appl. No.: 10/603,978

(22) Filed: Jun. 25, 2003

(65) Prior Publication Data

US 2004/0265432 A1 Dec. 30, 2004

(51) Int. Cl.
*A21D 8/04* (2006.01)
*A23L 1/01* (2006.01)

(52) U.S. Cl. .......................... 426/20; 426/52; 426/56; 426/64

(58) Field of Classification Search .................. 426/64, 426/20, 42, 56, 52, 10, 549, 615, 658, 438
See application file for complete search history.

(56) References Cited

U.S. PATENT DOCUMENTS

| 2,490,431 A | 12/1949 | Greene et al. |
| 2,704,257 A | 3/1955 | De Sollano et al. |
| 2,759,832 A | 8/1956 | Cording et al. |
| 2,780,552 A | 2/1957 | Willard et al. |
| 2,905,559 A | 9/1959 | Andersen et al. |
| 3,085,020 A | 4/1963 | Backinger et al. |
| 3,369,908 A | 2/1968 | Gonzales et al. |
| 3,690,895 A | 9/1972 | Amadon et al. |
| 3,917,866 A | 11/1975 | Purves et al. |
| 3,987,210 A | 10/1976 | Cremer |
| 3,998,975 A | 12/1976 | Liepa |
| 4,210,594 A | 7/1980 | Logan et al. |
| 4,985,269 A | 1/1991 | Irvin et al. |
| 5,356,646 A | 10/1994 | Simic-Glavaski et al. |
| 5,464,642 A | 11/1995 | Villagran et al. |
| 5,464,643 A | 11/1995 | Lodge |
| 5,558,886 A | 9/1996 | Martinez-Bustos et al. |
| 5,620,727 A * | 4/1997 | Gerrish et al. ............ 426/302 |
| 6,066,353 A | 5/2000 | Martines-Serna Villagran et al. |
| 6,068,873 A | 5/2000 | Delrue et al. |
| 6,287,622 B1 | 9/2001 | Martinez-Serna Villagran et al. |
| 6,383,533 B1 * | 5/2002 | Soeda et al. ................. 426/56 |
| 6,485,761 B1 * | 11/2002 | Xu .............................. 426/18 |
| 6,528,768 B1 | 3/2003 | Simic-Glavaski et al. |

FOREIGN PATENT DOCUMENTS

| EP | 000468731 A1 * | 1/1992 |
| WO | WO 96/01572 | 1/1996 |
| WO | WO 01/91581 | 12/2001 |
| WO | WO 04/04484 | 1/2004 |

OTHER PUBLICATIONS

FAO/WHO Consultation on the Health Implications of Acrylamide in Food: Summary Report: Geneva Switzerland, Jun. 25-27, 2002.
Talburt & Smith; "Potato Processing"; 4th Edition, 1987, pp. 535-646.
Watson, S.A.; "Com: Chemistry and Technology"; American Association of Cereal Chemists, 1987; pp. 410-420.
Zyzak, David et al.; "Acrylamide Formation Mechanism in Heated Foods"; Journal of Agricultural and Food Chemistry; vol. 51, No. 16, pp. 4782-4787, Jul. 2003.
Biederman, Maurus, et al.; "Methods for Determining the Potential of Acrylamide Formation and Its Elimination in Raw Materials for Food Preparation, such as Potatoes"; Official Food Control Authority of the Canton of Zurich, date n.a.
Biederman, Maurus, et al.: "Experiments on Acrylamide Formation and Possibilities to Decrease the Potential of Acrylamide Formation in Potatoes"; Official Food Control Authority of the Canton of Zurich, date n.a.
Nielson, Monk; "Enzyme Technology For Production of Protein Based Flavours"; Novo Nordisl; 1995.
www.Foodstandards.gov.uk; "Food Standards Agency Study of Acrylamide in Food Background Information and Research Findings"; Press Briefing May 17, 2002.
European Commission; health & Consumer Protection Directorate—General; "Opinion of the Scientific Committee on Food on new findings regarding the presence of acrylamide in food"; Jul. 3, 2002.
Institute of Food Science & Technology (UK); "Additional Research on Acrylamide in Food Essential, Scientists Declare"; Joint Press Release FAO/WHO/51; Jun. 27, 2002.

(Continued)

*Primary Examiner*—Keith Hendricks
(74) *Attorney, Agent, or Firm*—Bryn T. Lorentz; Melody A. Jones

(57) ABSTRACT

A method for the reduction of acrylamide in food products, food products having reduced levels of acrylamide, and an article of commerce. In one aspect, the method comprises reducing the level of reducing sugar in a food material before final heating (e.g., cooking). In another aspect, the method comprises adding to a food material an enzyme capable of reducing the level of reducing sugar. In yet another aspect, an article of commerce communicates to the consumer that a food product has reduced or low levels of acrylamide or reducing sugar.

9 Claims, 1 Drawing Sheet

OTHER PUBLICATIONS ww.cspinet.org; Center for Science in the Public Interest; "New Tests Confirm Acrylamide in American Foods"; Jun. 25, 2002.

Tareke, Eden, et al.; "Analysis of Acrylamide, a Carcinogen Formed in Heated Foodstuffs"; Journal of Agricultural and Food Chemistry, pp. A-I, date n.a.

Sanders, R.A. et al.; "An LC/MS Acrylamide Method and It's Use in Investigating the Role of Asparagine"; Presented at the Association of Analytical Communities; Sep. 2002.

Zyzak, David; "Acrylamide: Mechanism of Formation in Heated Foods": Presented to the FDA Food Advisory Committee; Feb. 24, 2003.

* cited by examiner

METHOD FOR REDUCING ACRYLAMIDE IN FOODS COMPRISING REDUCING THE LEVEL OF REDUCING SUGARS, FOODS HAVING REDUCED LEVELS OF ACRYLAMIDE, AND ARTICLE OF COMMERCE

FIELD OF INVENTION

The present invention relates to the reduction of acrylamide in food products and to food products having reduced levels of acrylamide. The invention further relates to an article of commerce.

BACKGROUND OF THE INVENTION

Since the dawn of civilization, carbohydrate-containing foods have been a staple in man's diet. Today, carbohydrate-containing foods such as breads, breakfast cereals, biscuits, crackers, cookies, French fries, cooked starchy vegetables, taco shells, and snack foods are popularly consumed. Although such foods have been part of the human diet for countless years, researchers have only recently discovered that many of these foods contain acrylamide.

In April 2002, the Swedish National Food Administration and researchers from Stockholm University announced their findings that acrylamide, a potentially cancer-causing chemical, is formed in many types of cooked foods. Acrylamide has a carcinogenic potency in rats that is similar to that of other carcinogens in food, but for humans, the relative potency in food is not known. Only limited human population data are available for acrylamide and these provide no evidence of cancer risk from occupational exposure. (*FAO/WHO Consultation on the Health Implications of Acrylamide in Food: Summary Report*; Geneva, Switzerland, 25–27 Jun. 2002.)

Although further research is needed to assess what health effects, if any, may result from human consumption of acrylamide at the levels commonly found in such foods, many consumers have voiced concern. Accordingly, it is an object of the present invention to provide a method for reducing the level of acrylamide in foods. It is also an object of the present invention to provide food products having reduced levels of acrylamide. Further, it is an object of the present invention to provide an article of commerce that communicates to the consumer that a food product has reduced or low levels of acrylamide.

SUMMARY OF THE INVENTION

In one aspect, the present invention provides a method for reducing the level of acrylamide in a food product. In one embodiment, the method comprises adding a reducing sugar-altering enzyme to the food material before heating.

In another aspect, the present invention provides a method for reducing the level of reducing sugars in a food material. In one embodiment, the method comprises adding a reducing sugar-altering enzyme to the food material before heating.

In another aspect, the present invention provides food products having reduced levels of acrylamide.

In yet another aspect, the present invention provides an article of commerce that communicates to the consumer that a food product has reduced or low levels of acrylamide or of reducing sugar.

All documents cited herein are, in relevant part, incorporated herein by reference; the citation of any document is not to be construed as an admission that it is prior art with respect to the present invention.

BRIEF DESCRIPTION OF THE DRAWINGS

FIG. 1 sets forth the proposed reaction mechanism by which acrylamide forms from asparagine and a carbonyl source (such as glucose). $R_1$ and $R_2$ can=H, $CH_3$, $CH_2OH$, $CH_2(CH_2)_nCH_3$, or any other component making up a reducing sugar; n can be any integer less than 10.

DETAILED DESCRIPTION OF THE INVENTION

Figure 1:
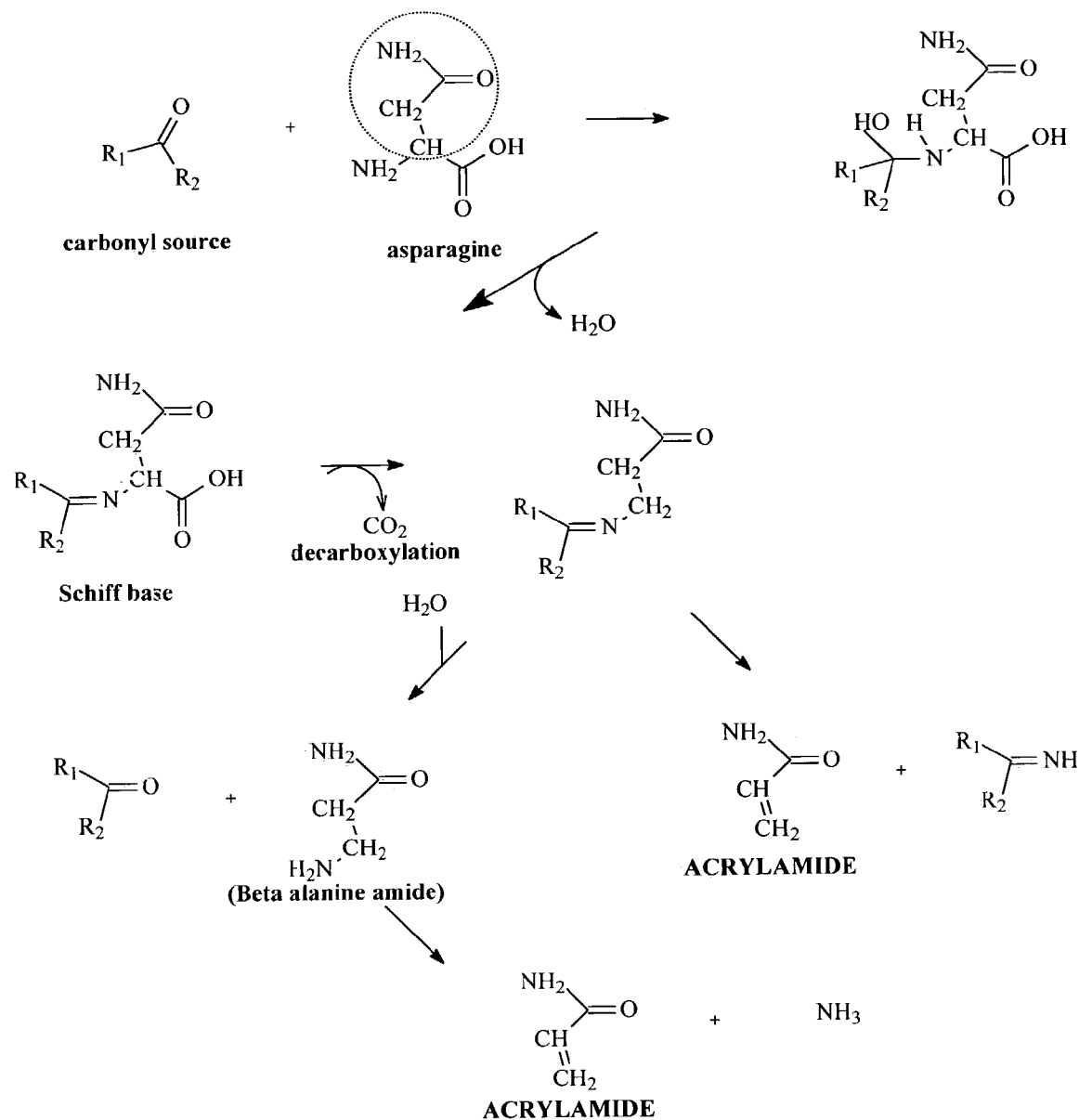
FIG. 1.

Applicants have discovered that foods containing reducing sugars and asparagine, a naturally occurring amino acid found in virtually all living systems, can form acrylamide when heated. Thus, foods richer in reducing sugars, when heated, tend to contain higher levels of acrylamide; this is especially the case when reducing sugar-containing foods are heated in the presence of foods containing higher levels of asparagine. Formation of acrylamide has also been found to be higher when foods are cooked to a lower final moisture content.

While not being limited by theory, it is believed that acrylamide forms in food products via the reaction mechanism set forth in FIG. 1. It is believed that the alpha-amine group of free asparagine reacts with a carbonyl source, forming a Schiff base. Under heat, the Schiff base adduct decarboxylates, forming a product that can either: (1) hydrolyze to form beta-alanine amide (which can, under heat, further degrade to form acrylamide) or (2) decompose to form acrylamide and the corresponding imine. (Applicants have discovered that the circled precursor atoms comprise the carbons and nitrogens in acrylamide.)

Accordingly, Applicants have further discovered that acrylamide formation in heated foods can be reduced by decreasing the amount of reducing sugar or converting the reducing sugar in the food to another substance before cooking. When such foods containing reduced levels of reducing sugar are heated, the amount of acrylamide formed is reduced.

Furthermore, Applicants have found that reducing the level of acrylamide in the finished food product can be accomplished by adding an enzyme that alters the reducing sugar ("reducing sugar-altering enzyme"). Preferably, the reducing sugar-altering enzyme catalyzes the oxidation or reduction of the reducing sugar prior to heating (e.g., cooking) the food. The mechanism by which reducing sugars are oxidized or reduced by enzymes are well known.

A preferred oxidizing enzyme for use in the method herein includes, but is not limited to, glucose oxidase. However, any enzyme capable of catalyzing the oxidation or reduction of the reducing sugar to prevent the formation of acrylamide is within the scope of the present invention.

The advantages of using enzymes in food processing are numerous. These advantages include: (a) they are natural, nontoxic substances; (b) they generally catalyze a given reaction without causing unwanted side reactions; (c) they are active under very mild conditions of temperature and pH; (d) they are active at low concentrations; (e) the rate of reaction can be controlled by adjusting temperature, pH, and the amount of enzyme employed; and (f) they can be inactivated after the reaction has proceeded to the desired extent. (*Food Chemistry*, 4th Ed., Owen R. Fennema, Ed., Marcel Dekker, Inc., New York, 1985, pp. 427, 433.)

A. Method for Reduction of Acrylamide in Food Products

In one aspect, the present invention provides a method for the reduction of acrylamide in a food product. In one embodiment, the method comprises reducing the level of reducing sugar in a food material before final heating (e.g., cooking). In another aspect, the method comprises adding to a food material an enzyme capable of catalyzing the oxidation or reduction of the carbonyl group of reducing sugar.

In another aspect, the present invention provides a method for the reduction of reducing sugar in a food product. In one embodiment, the method comprises adding to a food material an enzyme capable of catalyzing the oxidation or reduction of the reducing sugar. As used herein, the term "reducing sugar" refers to any carbohydrate found in food materials that can contribute a carbonyl group when reacting with asparagine to form acrylamide.

In a preferred embodiment, the present invention provides a method for reducing the level of acrylamide in food, comprising:

(1) adding a reducing sugar-altering enzyme to a food material, wherein said food material comprises reducing sugar;
(2) optionally mixing the enzyme with the food material;
(3) allowing a sufficient time for the enzyme to react with the reducing sugar;
(4) optionally deactivating or optionally removing the enzyme; and
(5) heating the food material to form the finished food product.

1. Adding a Reducing Sugar-Altering Enzyme to a Food Material, Wherein Said Food Material Comprises Reducing Sugar In a preferred embodiment, the reducing sugar-altering enzyme is an enzyme capable of catalyzing the oxidation or reduction of the carbonyl group of the reducing sugar. As used herein, "reducing sugar enzyme" or "reducing sugar-altering enzyme" or "enzyme" includes any enzyme capable of reducing the level of one or more reducing sugar in a food product. The reducing sugar-altering enzyme can include two classes of enzymes: oxidases and reductases, which catalyze either the oxidation or reduction of reducing sugars, respectively.

A preferred oxidizing enzyme for use herein is glucose oxidase. A preferred source of glucose oxidase is Sigma-Aldrich, catalog #G7141. Other oxidizing enzymes can include pyranose oxidase and aldose dehydrogenase.

A preferred reducing enzyme for use herein is aldose reductase.

As used herein, the term "reducing sugar enzyme" or "reducing sugar-altering enzyme" or "enzyme" includes one or more enzymes; for example, a mixture of two or more enzymes is encompassed by the terms.

The enzyme may be added to the food material in any suitable form. For instance, the enzyme may be added as a powder or in the form of a solution. Furthermore, the enzyme may be added to the food material in any suitable manner, such as directly (for example, sprinkled, poured, or sprayed on the food material) or indirectly. In one embodiment, the enzyme is admixed with a food that does not contain reducing sugar, then the resulting mixture is added to the reducing sugar-containing food. In another embodiment, at least a portion of the reducing sugar is extracted from the food material, the resulting extract is treated with the enzyme, then at least a portion of the extract is added back into at least a portion of the food material; for example, the enzyme may be added to the stream, or the stream may be pumped through a bed or column of immobilized enzyme (enzyme either adsorbed or chemically bonded to a substrate, preferably an inert substrate, e.g., pieces of plastic or beads in a column). As used herein, "adding" the enzyme to the food material includes, but is not limited to, any means of bringing the reducing sugar and the enzyme together.

In one embodiment where an oxidizing enzyme is used, such as glucose oxidase, the enzyme in the dominant bath converts reducing sugar to gluconolactone; this creates a driving force for additional reducing sugar extraction on subsequent additions of batches of food material. Extractable materials equilibrate with the food material such that additional soluble food material components do not extract out, except for reducing sugar, which continues to react and be converted by the enzyme. The gluconolactone that is formed from the reducing sugar soaks back into the food material and equilibrates. Additional solvent and/or enzyme-containing solution is added back after every batch of food material to make up for the solution that is removed by the previous batch of food material; this maintains a constant volume of the dominant bath. Alternatively, a reducing enzyme, such as aldose reductase, can be used to convert the reducing sugar to the reduced species. The use of a reductase is preferred because the resulting enzymatic product is a sugar that retains its sweetness.

The enzyme can be added to the food material at any suitable stage of the method. For example, the enzyme may be added with the other ingredients during the mixing of a dough.

As used herein, "food material" includes any type of reducing sugar-containing food, food product, food ingredient, or mixtures thereof, including any edible material used in the preparation of food. The food material can be in any suitable form, including raw or pre-treated. Suitable methods of pre-treating the food material include, but are not limited to, blanching, steaming, boiling, chopping, macerating, comminuting, reducing the particle size, drying with heat, and combinations thereof. For example, enzyme can be added to a food material before, during, or after maceration. In one embodiment, the food material is soaked in water before the enzyme is added.

Enzymes are marketed by units of activity, rather than by weight or volume. Thus, the effective amount of enzyme required to achieve the desired level of acrylamide reduction in the finished food product will depend upon the activity of the particular enzyme product used.

The amount of enzyme to add can depend upon the level of reducing sugar reduction, and accordingly the level of acrylamide reduction, that is desired. The amount of enzyme to add can also depend upon the amount of reducing sugar present in the food material; food materials higher in reducing sugar will generally require increased levels of enzyme or increased reaction time to achieve the same level of acrylamide reduction. The amount of enzyme to add can also depend upon the particular enzyme used (for example, the particular enzyme's ability to degrade reducing sugar) and the particular food material treated. One skilled in the art will be able to determine the effective amount of enzyme based upon the specific food material, the specific enzyme, the enzyme's specific activity, and the desired result.

2. Optionally Mixing the Enzyme with the Food Material

Optionally but preferably, the enzyme is thoroughly mixed with the food material. Any suitable method of mixing can be used. In one embodiment, mixing is carried out simultaneously with the maceration of the food material and the addition of the enzyme.

3. Allowing a Sufficient Time for the Enzyme to React with the Reducing Sugar

The amount of time needed for the enzyme to react with the reducing sugar will depend upon factors including, but not limited to, the desired level of acrylamide reduction, the characteristics of the particular food material (e.g., chemical composition, amount of reducing sugar present, particle size), and the particular enzyme added. Preferably, the enzyme is allowed to react for a sufficient amount of time to result in a food material wherein the level of reducing sugar has been reduced by at least about 10%, preferably at least about 30%, more preferably at least about 50%, still more preferably at least about 70%, and even more preferably at least about 90%. In general, the longer the enzyme is allowed to react, the greater the level of reducing sugar reduction and thus the greater the level of acrylamide reduction. The step of allowing a sufficient time for the enzyme to react can be carried out in any suitable manner; for example, it can be carried out simultaneously with adding the enzyme to the food material, mixing the enzyme with the food material, or combinations thereof.

As known in the art, pH and temperature are factors that affect enzymatic activity. One skilled in the art should readily be able to determine optimal conditions of these and other parameters (e g., water content). In addition, optimal pH and temperature conditions for specific enzymes are typically available in the literature and/or from enzyme suppliers.

4. Optionally Deactivating or Optionally Removing the Enzyme

After the enzyme has reacted to the desired extent, it can optionally be inactivated or removed from the food material. When an enzyme that is safe for consumption (e.g., naturally occurring and found in common foods) is used, one may choose not to deactivate or remove the enzyme. Alternatively, the enzyme can be deactivated by any suitable means that inactivates the enzyme. For example, the enzyme can be deactivated through the use of heat, pH adjustment, treatment with a protease, or combinations thereof. Furthermore, the enzyme can be removed from the food material by any suitable means including, but not limited to, extraction. The enzyme can be deactivated, removed, or subjected to a combination of deactivation and removal.

5. Heating the Food Material to Form the Finished Food Product

The food material can then be heated in the usual manner, such as by baking, frying, extruding, drying (e.g., via vacuum oven or drum dryer) puffing, or microwaving. At least a portion of the enzyme may be added to the food material during the heating step. Deactivating the enzyme may occur through heating, thus the optional deactivation step and the cooking step may be carried out simultaneously. Heat processing via cooking can denature and inactivate the enzyme such that the food material is not subjected to continuing enzymatic activity. Furthermore, at least a portion of the time allowed for enzymatic reaction may be carried out during the heating step.

As used herein the term "finished food product" or "food product" includes, but is not limited to, foods ready for consumption and foods to be used as ingredients to prepare other foods.

Preferably, the level of acrylamide in the finished food product is reduced by at least about 10%, preferably at least about 30%, more preferably at least about 50%, still more preferably at least about 70%, and even more preferably at least about 90%.

B. Means of Practicing the Method

The present invention can be practiced by any suitable means. For example, the method herein can be practiced in batch, semi-batch, or continuous mode.

C. Food Products Having Reduced Levels of Acrylamide

Food products prepared according to the method herein can have a reduction in the acrylamide level of at least about 10%, preferably at least about 30%, more preferably at least about 50%, still more preferably at least about 70%, and even more preferably at least about 90%.

The method herein can be applied to the production of any suitable food product, including but not limited to carbohydrate-containing foods, especially low-moisture foods (e.g., less than about 10%), that are heated during preparation. For instance, the method can be used to reduce the level of acrylamide found in mashed potatoes, potato chips, fabricated snack foods, French fries, breakfast cereals, breads, cookies, crackers, toaster pastries, pizza crust, pretzels, hash browns, tater tots, corn tortillas, and taco shells.

In one embodiment, fried fabricated potato crisps have less than about 400 ppb acrylamide, preferably less than about 300 ppb, more preferably less than about 200 ppb, still more preferably less than about 50 ppb, and most preferably less than about 10 ppb.

In yet another embodiment, French fries made from cut potatoes have less than about 40 ppb acrylamide, preferably less than about 30 ppb, more preferably less than about 20 ppb, and most preferably less than about 10 ppb.

In a particular embodiment, potato chips made according to the method herein can have less than about 150 ppb acrylamide, preferably less than about 100 ppb, more preferably less than about 50 ppb, even more preferably less than about 10 ppb, and most preferably less than about 5 ppb.

In still another embodiment, tortilla chips and corn chips have less than about 75 ppb acrylamide, preferably less than about 50 ppb, and more preferably less than about 10 ppb.

Although the method herein will generally be described in terms of preferred potato food products and tortilla chips, it should be understood by one skilled in the art that the method herein can be applied to any suitable food product. Non-limiting examples include crackers, breads (e.g., rye, wheat, oat, potato, white, whole grain products, mixed flours, loaves, twists, buns, rolls, pitas, matzos, foccoccia, melba toast, zwieback, croutons, soft pretzels, soft and hard bread sticks, heat and serves), toaster pastries, cookies, danish, croissant, tarts, pie crusts, pastries, muffins, brownies, sheet cakes, donuts, snack foods (e.g., pretzels, tortilla chips, corn chips, potato chips, fabricated snacks, fabricated potato crisps, extruded snacks, extruded filled snacks, trail mix, granola, snack mixes, shoe-string potatoes), flours, mixes (e.g., cake mixes, biscuit mixes, brownie mixes, bread mixes, pancake mixes, crepe mixes, batter mixes, pizza dough), refrigerated doughs (e.g., biscuits, breads, bread sticks, croissants, dinner rolls, pizza dough, cookies, danish, brownies, pie crust), frozen foods (pie crusts, pies, tarts, turnovers, pizzas, food pockets, cakes, French fries, hash browns, breaded products such as chicken and fish, breaded vegetables), bagels, breakfast cereals, biscuits, French fries, vegetables (e.g., dried, grilled, roasted, broiled, fried, vacuum dried), taco shells, hash browns, mashed potatoes, toast, grilled sandwiches, flour and corn tortillas, crepes, pancakes, waffles, batters, pizza crust, rice, nut-based foods (e.g, peanut butter, foods containing chopped nuts), fruit (e.g., dried, grilled, roasted, broiled, fried, vacuum dried, jellies, baked, pie fillings, flambés, raisins), hush puppies, alcoholic beverages (e.g., beers and ales), products comprising roasted cocoa beans (e.g., chocolates, confectionary coatings, hot chocolate, hot chocolate mixes), and animal foods (e.g., dog food, cat food, ferret food, guinea pig food, rabbit food, rat food, mouse food, chicken food, turkey food, pig food, horse food, goat food, sheep food, monkey food, fish food).

1. Dehydrated Potato Products

The present invention can be used to make dehydrated potato products having reduced levels of acrylamide. The following sets forth a preferred method of making such dehydrated potato products, but the present invention is not limited to this particular embodiment. Although the embodiment set forth in detail below describes addition of enzyme before the cooked potatoes are comminuted, it should be understood that enzyme may be added at any suitable stage of any suitable process for making dehydrated potato products. For instance, enzyme may be added to the potatoes before cooking, after cooking, before comminution, after comminution, or during any other suitable processing step before the final dehydrated potato product is formed. Furthermore, non-limiting examples of other embodiments may comprise: (a) adding enzyme to raw potato followed by conventional dehydrated potato processing, (b) adding enzyme to raw potato followed by shredding or thinly slicing and conventional processing, (c) adding enzyme to raw potato followed by shredding or thinly slicing, then blanching, then followed by conventional processing, (d) adding enzyme to blanched, shredded, or thinly sliced potato followed by conventional processing, or (e) any other suitable means of adding enzyme. The method herein may also be practiced with any suitable method for making dehydrated potato products known in the art, such as those set forth in *Potato Processing*, 4$^{th}$ Ed., Talburt and Smith, Eds., AVI Books, Van Nostrand Reinhold Co., New York, 1987, [hereinafter "*Potato Processing*"], at pp. 535–646.

In a preferred embodiment, dehydrated potato products, such as potato flakes, flanules, or granules, can be made in accordance with the following method. In general, the method comprises: (1) cooking potatoes; (2) adding a reducing sugar-altering enzyme to the cooked potatoes; (3) forming a wet mash; and (4) drying the mash to form dehydrated potato products.

Any suitable potatoes, such as those used to prepare conventional potato flakes, flanules, or granules, can be used to prepare the dehydrated potato products herein. Preferably, the dehydrated potato products are prepared from potatoes such as, but not limited to, Norchip, Norgold, Russet Burbank, Lady Rosetta, Norkotah, Sebago, Bintje, Aurora, Saturna, Kinnebec, Idaho Russet, Altura, Russet Norkotah, Atlantic, Shepody, Asterix, and Mentor.

The potatoes are subjected to cooking to soften them for mashing. The potatoes may be peeled, partially peeled, or unpeeled. The potatoes may be whole or may be sliced into pieces of any size before cooking. The cooking procedure can be any thermal or other type of cooking process that softens the potatoes for mashing. For instance, the potatoes may be cooked by submersion in water or steam.

For example, potato slices having an average thickness of about ⅜ inch to about ½ inch are typically cooked with steam having a temperature of from about 200° F. (93° C.) to about 250° F. (121° C.) from about 12 to about 45 minutes, more particularly from about 14 to about 18 minutes. Shoestring cut potatoes pieces are typically cooked with steam having a temperature of from about 200° F. (93° C.) to about 250° F. (121° C.) for about 7 to about 18 minutes, more particularly from about 9 to about 12 minutes, to achieve the desired softness.

Next, an effective amount of enzyme, preferably glucose oxidase, is added to the cooked potatoes. Depending upon the functional temperature range of the enzyme used, the cooked potatoes may first require temperature adjustment before addition of the enzyme. The cooked potatoes are then comminuted to produce a wet mash. Comminution of the cooked potatoes may be accomplished by any suitable means, such as but not limited to ricing, mashing, shredding, or a combination thereof.

Optional ingredients can be added and mixed into the wet mash. Such optional ingredients can include starch. Starch can include, but is not limited to, any suitable native or modified starch, including any dried potato products that are added into or back into the mash. Emulsifier can also optionally be added to the wet mash as a processing aid.

After the mash is formed, it can be further dried and processed as described below to form dehydrated potato products. Alternatively, the wet mash can be used to produce products such as, but not limited to, mashed potatoes, potato patties, potato pancakes, and potato snacks such as extruded French fries, potato sticks, and snack chips.

For example, the wet potato mash can be used to produce extruded French fried potato products such as those described in U.S. Pat. No. 3,085,020, issued Apr. 9, 1963 to Backinger et al.

After forming the mash, the mash is dried to form dehydrated potato products. These dehydrated potato products can be in any form, such as but not limited to flakes, flanules, granules, agglomerates, sheets, pieces, bits, flour, or particulates.

Any suitable procedure, such as those known in the art, for producing such dehydrated potato products from a mash may be employed, and any suitable equipment may be used. For example, the mash can be dried to produce flakes according to known processes such as those described in U.S. Pat. No. 6,066,353, issued May 23, 2000 to Villagran, et al., as well as those processes described in U.S. Pat. No. 2,759,832 issued Aug. 19, 1956 to Cording et al., and U.S. Pat. No. 2,780,552 issued Feb. 5, 1957 to Willard et al. The mash can be dried to make flanules according to the process set forth in U.S. Pat. No. 6,287,622, issued Sep. 11, 2001 to Villagran et al. Granules can be produced by processing the mash according to the process described in U.S. Pat. No. 3,917,866, issued Nov. 4, 1975 to Purves et al., or by other known processes such as that described in U.S. Pat. No. 2,490,431 issued Dec. 6, 1949 to Greene et al. Suitable dryers can be selected from those well known drying devices including but not limited to fluidized bed dryers, scraped wall heat exchangers, drum dryers, freeze-dryers, air lift dryers, and the like.

Preferred drying methods include those that reduce the amount of total thermal input. For example, freeze drying, drum drying, resonant or pulse flow drying, infrared drying, or a combination thereof is preferred when producing flakes; and air lift drying, fluidized bed drying, or a combination thereof is preferred when producing granules.

Although the dehydrated potato products herein will be primarily described in terms of flakes, it should be readily apparent to one skilled in the art that the potato mash of the present invention can be dehydrated to produce any desired dehydrated potato product that can be derived from a mash.

Drum drying, such as with drum dryers commonly used in the potato product industry, is the preferred method for drying the potato mash to form flakes. The preferred process utilizes a single drum drier wherein the wet potato mash is spread onto the drum in a thin sheet having a thickness of from about 0.005" to about 0.1", preferably from about 0.005" to about 0.05", more preferably about 0.01". Typically, when a drum dryer is used, the mash is fed to the top surface of the drum by a conveying means. Small diameter unheated rolls progressively apply fresh potato mash to portions already on the drum, thus building up a sheet, or layer, having a predetermined thickness. The peripheral speed of the small rolls is the same as that of the drum. After the layer of mash travels around a portion of the circumference of the drum, a doctor knife removes the dried sheet by peeling the dried sheet away from the drum. Typically, the drum dryer itself is heated to temperatures in a range of from about 250° F. (121° C.) to about 375° F. (191° C.), preferably from about 310° F. (154° C.) to about 350° F. (177° C.), and more preferrably from about 320° F. (160° C.) to about 333° F. (167° C.) by pressurized steam contained within the drum at pressures of from about 70 psig to about 140 psig. For best results, the rotational speed of the dryer drum and the internal temperature thereof are suitably controlled so as to give a final product having a moisture content of from about 5% to about 14%, preferably from about 5% to about 12%. Typically, a rotational speed of from about 9 sec/rev to about 25 sec/rev., preferably about 11 sec/rev to about 20 sec/rev, is sufficient.

Once the wet mash is sheeted and dried, the resulting dried sheet of flakes can then be broken into smaller sections if desired. These smaller sections can be of any desired size. Any method of breaking the sheet that minimizes starch and potato cell damage, such as fracturing, grinding, breaking, cutting, or pulverizing, can be used. For example, the sheet can be comminuted with an Urschel Comitrol™, manufactured by Urschel Laboratories, Inc. of Valparaiso, Ind., to break up the sheet. Alternatively, the sheet of flakes can be left intact. As used herein, both the intact sheet of flakes and smaller sheet sections are included in the term "potato flakes."

2. Foods Made from Dehydrated Potato Products

The dehydrated potato products can be used to make any suitable food product. An especially preferred use of the dehydrated potato products is in the production of fabricated snacks made from a dough, preferably fabricated chips. Examples of such fabricated chips include those described in U.S. Pat. No. 3,998,975 issued Dec. 21, 1976 to Liepa, U.S. Pat. No. 5,464,642 issued Nov. 7, 1995 to Villagran et al., U.S. Pat. No. 5,464,643 issued Nov. 7, 1995 to Lodge, and WO 96/01572 published Jan. 25, 1996 by Dawes et al.

In one embodiment, the fabricated snack is made by the method comprising:
(1) adding a reducing sugar-altering enzyme to a dough;
(2) forming a snack piece from the dough; and
(3) cooking the snack piece to form a fabricated snack.

Cooking can be performed by any suitable method, for instance by frying, baking, or a combination of frying or baking. Furthermore, the forming and cooking steps can be carried out simultaneously, such as with extruded snack products.

In another embodiment, the fabricated snack is made by the method comprising:
(1) blending dry ingredients;
(2) optionally adding emulsifier to dry ingredients;
(3) adding water;
(4) mixing to form a dough;
(5) forming a dough sheet;
(6) forming a snack piece from the dough sheet; and
(7) cooking the snack piece to form a fabricated snack.

Enzyme can be added at any suitable stage of the process, for instance enzyme may be added during the blending, optionally adding emulsifier, adding water, mixing, and/or forming steps. Alternatively, the enzyme can be applied, preferably as a solution, to the dough surface; this can occur either before or after the snack pieces are formed from the dough sheet. In one embodiment, the enzyme solution is added to the surface of the dough sheet.

The dehydrated potato products can also be rehydrated and used to produce food products such as mashed potatoes, potato patties, potato pancakes, and other potato snacks such as extruded French fries and potato sticks. For example, dehydrated potato products can be used to produce extruded French fried potato products such as those described in U.S. Pat. No. 3,085,020, issued Apr. 9, 1963 to Backinger et al., and U.S. Pat. No. 3,987,210, issued Oct. 18, 1976 to Cremer. The dehydrated potato products can also be used in breads, gravies, sauces, baby food, or any other suitable food product.

3. Potato Chips

The present invention can be used to make potato chips having reduced levels of acrylamide. The following sets forth a preferred method of making such potato chip products, but the present invention is not limited to this particular embodiment. For example, enzyme may be added at any suitable processing stage of art-recognized potato-chipping methods, such as those set forth in *Potato Processing*, at pp. 371–489.

In a preferred embodiment, the present invention provides a method for reducing the level of acrylamide in potato chips, comprising:
(1) optionally peeling potatoes;
(2) optionally washing potatoes;
(3) slicing potatoes to form potato slices;
(4) optionally rinsing the potato slices;
(5) optionally blanching the potato slices;
(6) optionally cooling the potato slices;
(7) adding a reducing sugar-altering enzyme to the potato slices;
(8) optionally drying the potato slices;
(9) frying the potato slices to form potato chips.

Most preferably, the potato slices are blanched before the enzyme is added. Although the foregoing describes addition of enzyme at step (7) above, it should be understood that enzyme may be added at any suitable stage of the process. For instance, enzyme may be added to the potatoes before slicing, after slicing, after rinsing, during blanching, during cooling, or at any other suitable stage before drying, if the optional drying step is performed, or at any other suitable stage before frying if the potato slices are not optionally dried.

In another embodiment, potato slice blanching and soaking solutions containing reducing sugar are pumped through a column containing immobilized enzyme. The effluent from the column is returned to the potato slices. The potato slices are then processed according to typical processing procedures. Practicing the method in this manner can return at least part of the native potato flavors back to the chip that may be lost during the blanching and enzyme treatment steps.

Potato chips made according to the method herein can have less than about 150 ppb acrylamide, preferably less than about 100 ppb, more preferably less than about 50 ppb, even more preferably less than about 10 ppb, and most preferably less than about 5 ppb.

4. French Fries

The present invention can be used to make French fries having reduced levels of acrylamide. The following sets forth a preferred method of making such French fries, but the present invention is not limited to this particular embodiment. For example, enzyme may be added at any suitable processing stage of art-recognized methods for making French fries, such as those set forth in *Potato Processing*, at pp. 491–534, or those methods described in U.S. Pat. Nos. 6,001,411 and 6,013,296.

In a preferred embodiment, the present invention provides a method for reducing the level of acrylamide in French-fries, comprising:

(1) optionally peeling potatoes;
(2) optionally washing potatoes;
(3) cutting potatoes to form potato strips;
(4) optionally rinsing the potato strips;
(5) optionally blanching the potato strips;
(6) optionally cooling the potato strips;
(7) adding a reducing sugar-altering enzyme to the potato strips;
(8) optionally drying the potato strips;
(9) optionally coating the potato strips; and
(10) par-frying the potato strips to form par-fries.

The par-fries can then be frozen, packaged, and stored for later frying to form the final French fries.

Most preferably, the potato strips are blanched before the enzyme is added. If coated French fries are desired, a suitable coating material, such as starch or a blend of materials comprising one or more starches, can be used to coat the potato strips before par-frying. Although the foregoing describes addition of enzyme at step (7) above, it should be understood that enzyme may be added at any suitable stage of the process. For instance, enzyme may be added to the potatoes before cutting, after cutting, after rinsing, during blanching, during cooling, or at any other suitable stage before drying, if the optional drying step is performed, or at any other suitable stage before par-frying if the potato strips are not optionally dried. Although less preferred, enzyme may be added between the steps of par-frying and final frying to form the final French fries.

Finished French-fries made from the par-fries of the present invention can have less than about 40 ppb acrylamide, preferably less than about 30 ppb, more preferably less than about 20 ppb, and most preferably less than about 10 ppb.

5. Tortilla Chips

Tortilla chips are particularly popular consumer snack products. Tortilla chips are traditionally made from whole kernel corn that has been cooked in a hot lime solution for about 5 to about 50 minutes, then steeped overnight. The cooking-steeping process softens the outer hull and partially gelatinizes the starch in the endosperm of the corn. This cooked-steeped corn, called "nixtamal," is then washed to remove the outer hull and ground to form a plastic dough, known as "masa," that contains about 50% moisture. The freshly-ground masa is sheeted, cut into snack pieces, and baked for about 15 to about 30 seconds at a temperature of from about 575° F. to about 600° F. (302° C. to 316° C.) to reduce the moisture content to from about 20% to about 35%. The baked snack pieces are then fried in hot oil to form tortilla chips having a moisture content of less than about 3%. See, e.g., U.S. Pat. No. 2,905,559, issued Nov. 1, 1958 to Anderson et al., U.S. Pat. No. 3,690,895, issued Sep. 12, 1972 to Amadon et al., and *Corn: Chemistry and Technology*, American Association of Cereal Chemists, Stanley A. Watson, et. al., Ed., pp. 410–420 (1987).

Tortilla chips can also be made from dried masa flour. In typical processes for making such dried masa flour, such as those described in U.S. Pat. No. 2,704,257 issued Mar. 1, 1955, to de Sollano et al., and U.S. Pat. No. 3,369,908, issued Feb. 20, 1968 to Gonzales et al., the lime-treated corn is ground and dehydrated to a stable form. The dried masa flour can be later rehydrated with water to form a masa dough that is then used to produce tortilla chips, such as those described in WO 01/91581, published Dec. 6, 2001, by Zimmerman et al.

In one embodiment, a tortilla chip made from masa is made by the method comprising:

(1) adding a reducing sugar-altering enzyme to a dough comprising masa;
(2) forming a snack piece from the dough; and
(3) cooking the snack piece to form a tortilla chip.

In another embodiment, a tortilla chip made from nixtamal is made by the method comprising:

(1) adding a reducing sugar-altering enzyme to nixtamal;
(2) forming a snack piece from the nixtamal; and
(3) cooking the snack piece to form a tortilla chip.

Enzyme can be added at any suitable stage of the process. In one embodiment, the enzyme solution is added to the surface of the dough sheet.

Cooking can be performed by any suitable method, for instance by frying, baking, or a combination of frying or baking. Furthermore, the forming and cooking steps can be carried out simultaneously, such as by extrusion.

In one another embodiment, the tortilla chips comprise less than about 75 ppb acrylamide, preferably less than about 50 ppb, and more preferably less than about 10 ppb. In another embodiment, corn chips made by the method herein comprise less than about 75 ppb acrylamide, preferably less than about 50 ppb, and more preferably less than about 10 ppb.

D. Article of Commerce

Another embodiment of the invention is an article of commerce comprising:

(a) a food product, wherein said food product has a reduced level of acrylamide;
(b) a container for containing the food product; and
(c) a message associated with the container.

The message informs the user that the food product contains a reduced level of acrylamide. The message can be printed material attached directly or indirectly to the container, attached directly or indirectly near the container, or alternatively can be a printed, electronic, or broadcast message associated with the food product or with the container.

In one embodiment of the present invention, a food product having reduced levels of acrylamide is provided in a container having a message associated therewith. Any container from which the food product can be dispensed, presented, displayed, or stored is suitable. Suitable containers include, but are not limited to, bags, canisters, boxes, bowls, plates, tubs, and cans.

The message informs the consumer that the food product contains a reduced level of acrylamide. The message can be printed material attached directly or indirectly to the container, attached directly or indirectly near the container, or alternatively can be a printed, electronic, or broadcast message associated with the food product or with the container. Suitable messages include, but are not limited to, messages that communicate "reduced" or "low" levels of acrylamide, messages that communicate that less than a specified amount of acrylamide is present (e.g., less than 5 ppb), and messages that communicate that the food product meets or exceeds a suggested or mandatory level (e.g., regulatory threshold or signal level).

In another embodiment, the message informs the consumer that the food product is made with an ingredient or ingredients with reduced or low levels of reducing sugar.

Analytical Methods

Parameters used to characterize elements of the present invention are quantified by particular analytical methods. These methods are described in detail as follows.

1. Acrylamide

Method for Measuring Acrylamide (AA) in Food Products

Summary

Food products are spiked with 1-$^{13}$C-acrylamide ($^{13}$C-AA) and extracted with hot water. The aqueous supernatant is extracted three times with ethyl acetate, and the ethyl acetate extracts are combined and concentrated and analyzed by LC/MS with selected ion monitoring for specific detection of AA and $^{13}$C-AA.

Extraction of Sample

1. Weigh 6.00±0.01 g of sample into a 125-mL Erlenmeyer flask. Note: Place the sample into a food processor and pulse for 30 seconds so that the particle size is about ⅛ inch or less. If the sample is too small to be effectively ground in a food processor, place the sample in a new plastic bag (e.g., Whirl-Pak™ or equivalent) and pulverize with a rubber mallet until the particle size is ⅛ inch or less.
2. Add 120 μL of 100 ng/μL $^{13}$C-AA in de-ionized distilled water (ISTD 2), with an adjustable 1000-μL pipette (calibrated), directly onto the sample.
3. Using a dispenser, add 40 mL of de-ionized distilled water to the flask and cover with foil.
4. Place into a 65° C. water bath for 30 min.
5. With a dispenser, add 10 mL of ethylene dichloride to the flask, and homogenize with a Tekmar Tissumizer™ (SDT-1810) or Ultra-Turrax® (T18 Basic) for 30 seconds, or until uniform. Rinse the probe into the flask with deionized distilled water.
6. Place 25 g of the homogenate into an 8-dram vial
7. Tightly cap the tube and centrifuge for 30 minutes at 2500–5200 RPM.
8. Transfer 8 g of supernatant to another 8-dram vial being careful to avoid solid particles.
9. Add 10 mL of ethyl acetate with a dispenser, cap, and vortex for 10 seconds.
10. Allow any emulsion to break up; help by swirling or shaking once or twice and then allowing layers to split.
11. Transfer as much of the top layer (ethyl acetate) as possible to a scintillation vial, without transferring any liquid (water) from the interface. Extract twice more with 5-mL portions of ethyl acetate and add to the same scintillation vial. Then, add approximately 2 g of anhydrous sodium sulfate.
12. Concentrate the extract with a gentle stream of nitrogen in a 60–65° C. water bath to about 1 mL. Transfer the extract to a Pierce REACTI-VIAL™ or equivalent conical-shaped glass vial and further concentrate the extract to a final volume of approximately 100–200 μL. Place this extract into an autosampler vial with a conical sleeve.

Preparation of Standards

Stock Solutions and Internal Standards

| Solution | Weight | Volumetric Flask | Solvent | Concentration (ppm) |
|---|---|---|---|---|
| Stock 1 | 0.1000 g Acrylamide (AA) | 100-mL | Ethyl Acetate | 1000 |
| ISTD 1 | 0.0100 g $^{13}$C-Acrylamide | 100-mL | Ethyl Acetate | 100 |
| Stock 2 | 0.1000 g Acrylamide (AA) | 100-mL | Deionized Distilled Water | 1000 |
| ISTD 2 | 0.0100 g $^{13}$C-Acrylamide | 100-mL | Deionized Distilled Water | 100 |

Intermediate Standards

| Solution | Volume Stock 1 AA (μL) | Volumetric Flask (mL) | Solvent | Concentration (ppm) |
|---|---|---|---|---|
| INT 1 | 100 | 10 | Ethyl Acetate | 10 |
| INT 2 | 1000 | 10 | Ethyl Acetate | 100 |

Calibration Standards

| Standard | Volume INT 1 (μL) | Volume INT 2 (μL) | Volume ISTD 1 (μL) | Volumetric Flask (mL) | Solvent | Conc. AA (ppm) | Conc. ISTD 1 (ppm) |
|---|---|---|---|---|---|---|---|
| 0 | 0 | 0 | 450 | 10 | Ethyl Acetate | 0 | 4.50 |
| 0.25 | 250 | 0 | 450 | 10 | Ethyl Acetate | 0.250 | 4.50 |
| 0.75 | 750 | 0 | 450 | 10 | Ethyl Acetate | 0.750 | 4.50 |
| 1.5 | 0 | 150 | 450 | 10 | Ethyl Acetate | 1.50 | 4.50 |
| 3.0 | 0 | 300 | 450 | 10 | Ethyl Acetate | 3.00 | 4.50 |
| 5.0 | 0 | 500 | 450 | 10 | Ethyl Acetate | 5.00 | 4.50 |

Homogenizer Cleaning Procedure

Use this cleaning procedure between every sample.
1. Fill a 1-L Erlenmeyer flask with hot tap water (≈80% full) and add a drop of Dawn™ dishwashing liquid (available from the Procter & Gamble Co.) or equivalent.
2. Insert the dispersing element probe into the water as far as possible.
3. Homogenize the solution for about 10–15 seconds.
4. Empty the cleaning solution from the Erlenmeyer; rinse and refill the flask with hot tap water.
5. Homogenize again for about 10–15 seconds.
6. Empty the flask and refill with hot tap water; homogenize again for about 10–15 seconds.
7. If the water is not clear and free of particulates, continue homogenizing clean hot tap water as many times as necessary to achieve this condition.
8. When the hot tap water is clear and free of particulates, rinse the probe with deionized distilled water.

Analysis by LC/MS

Samples are analyzed using a Waters 2690 LC interfaced to a Micromass LCZ mass spectrometer.

| | |
|---|---|
| Mobile Phase | 100% $H_2O$, 10 mM $NH_4Ac$, adjusted to pH 4.6 w/formic acid |
| Column | 2.0 mm × 150 mm, YMC C18 AQ (available from Waters Corp.) |
| Flow rate | 0.2 mL/min |
| Interface | Direct (no split) |
| Injection volume | 5 μL |
| MS ionization mode | Electrospray, positive ion mode |
| MS detection mode | Selected ion monitoring: m/z 72 (AA), m/z 73 ($^{13}$C-AA); dwell times: 0.5 s |

Data Analysis

Response ratios (area of AA peak/area of $^{13}$C-AA peak) are plotted against the corresponding concentration ratios for a series of five standards in ethyl acetate. All standards contain 4.5 μg/mL $^{13}$C-AA, and AA concentrations ranging from 0 to 5 μg/mL. Linear regression results in a calibration curve from which concentration ratios in extracts are determined from measured response ratios. When this concentration ratio is multiplied by the accurately known $^{13}$C-AA level (nominally 2 ppm) added to sample in step two of the extraction procedure, the level of AA in ppm results.

Sample Calculation for LC/MS:

The calibration curve is generated by plotting the response ratio (area m/z 72/area m/z 73) on the y axis vs. the concentration ratio ([AA]/[13C-AA]) on the x-axis. For this example, the equation of that line is y=0.899x+0.0123.

Measured area of AA peak (m/z 72) at 4.0 min: 100,000

Measured area of 13C-AA peak (m/z 73) at 4.0 min: 500,000

Response ratio $R_r$=0.200. From the slope and intercept of the calibration curve, the concentration ratio $R_c$ is calculated: $R_c$=(0.200−0.0123)/0.899=0.209

Given the spike level of 13C-AA in the sample (2 ppm), the measured level of AA is 0.209×2 ppm=0.418 ppm Quality Assurance/Quality Control (QA/QC)

1. All balances used in the preparation of standards and/or samples, must have their calibrations checked weekly with a set of qualified weights. The balances should be checked with at least three weights covering the range of sample/standard weights to be measured.
2. A six-point calibration curve should be performed daily.
3. A working reference material (WRM) should be analyzed with each set of samples. The concentration of this material should be within 2σ of the running mean. If it is not, the instrument should be recalibrated and the WRM recalculated.

2. % Reduction of Acrylamide

% Reduction Acrylamide=[(Acrylamide level in control sample−Acrylamide level in enzyme-treated sample)/Acrylamide level in control sample] ×100.

The control sample is prepared in exactly the same manner as the enzyme-treated sample, with the exception that enzyme is not added.

EXAMPLES

The following examples are illustrative of the present invention but are not meant to be limiting thereof.

Example 1

Dehydrated Potato Product

Russet baking potatoes are peeled, cut into ⅜ inch thick slabs, rinsed with water then placed in a pot of boiling water. The potatoes are boiled (submerged) for 20 minutes. The boiled potatoes are removed from the water and mashed.

500 units of glucose oxidase (purchased from Sigma-Aldrich catalog #G7141) are added to 45 ml of water, then added to 15 g of mashed potatoes and thoroughly admixed. The mixture is allowed to incubate for 30 minutes.

After the 30-minute incubation, the product is microwaved (Panasonic microwave, model NN-S5488A) on high for 2-minute increments for a total of 10 minutes until dry (and brown). Compared to dehydrated potato products prepared by the exact same process but without the enzyme (control sample), the enzyme-treated dehydrated potato product results in greater than a 10% reduction in acrylamide when analyzed for acrylamide using the method set forth herein.

Example 2

Potato Chips

Potato chips having reduced levels of acrylamide can be made using raw potato slices. Peel Atlantic potatoes and slice to ~1.1 mm thickness. Rinse and pad dry. Blanch potato slices in 165° F. water for fifteen seconds. Cool and drain blanched slices. Soak 100 grams of blanched potato slices in 250 ml of distilled/deionized water containing glucose oxidase, having 1000 units of activity, for one hour. Agitate sample by swirling for 1 minute every 8 minutes. Remove potato slices from the solution and blot dry on paper towels. Fry the potato slices in a fryer set at 375° F. for 60 seconds. Compared to; potato chips prepared by the exact same process but without enzyme addition (control sample), the enzyme-treated potato chips result in greater than a 10% reduction in acrylamide when analyzed for acrylamide using the method set forth herein.

Example 3

French Fries

French fries having reduced levels of acrylamide can be made using raw potato strips. Peel Atlantic potatoes and cut into strips having a cross-sectional area of about 8 mm×8 mm. Rinse and pad dry. Blanch potato strips in 165° F. water for one minute. Cool and drain blanched strips. Soak 100 grams of blanched potato strips in 250 ml of distilled/deionized water containing glucose oxidase, having 100 units of activity, for one hour. Agitate sample by swirling for 1 minute every 8 minutes. Fry the treated potato strips in a fryer set at 375° F. for 60 seconds to form French fries.

Compared to French fries prepared by the exact same process but without enzyme addition (control sample), the enzyme-treated French fries result in greater than a 10% reduction in acrylamide when analyzed for acrylamide using the method set forth herein.

Example 4

Article of Commerce

The potato chips of Example 2 are packaged in a bag for sale to consumers. Printed on the bag is a message stating, "Acrylamide-free product!"

Example 5

Article of Commerce

The potato chips of Example 2 are packaged in a bag for sale to consumers. Printed on the bag is a message stating, "Low in acrylamide!"

Example 6

Article of Commerce

The potato chips of Example 2 are packaged in a bag for sale to consumers. Printed on the bag is a message stating, "Acrylamide reduced by over 90%!" A television commercial for the chips communicates the message, "Our chips are lower in acrylamide!"

Example 7

Article of Commerce

Uniformly-shaped fabricated potato crisps having less than 100 ppb acrylamide are packaged in a cylindrical canister for sale to consumers. A television commercial for the crisps communicates the message, "Acrylamide-reduced!"

Example 8

Article of Commerce

The French fries of Example 3 are packaged in a paper sleeve having an open end, from which the fries protrude, for sale to consumers. A sign posted inside the retail establish where the French fries are sold reads, "Our fries contain reduced levels of acrylamide!"

Example 9

Article of Commerce

The French fries of Example 3 are packaged in a paper sleeve having an open end, from which the fries protrude, for sale to consumers. A sign posted inside the retail establish where the French fries are sold reads, "Our fries are lower in acrylamide!"

Example 10

Article of Commerce

The potato chips of Example 2 are packaged in a bag for sale to consumers. Printed on the bag is a message stating, "Made from ingredients low in reducing sugar!"

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for reducing the level of acrylamide in a food material, comprising reducing the level of reducing sugar in the food material before heating whereby a reducing sugar-altering enzyme comprising aldose reductase is added to the food material to reduce the level of reducing sugar.

2. The method of claim 1, wherein said method further comprises adding glucose oxidase, pyranose oxidase, aldose dehydrogenase, or a mixture thereof, to the food material.

3. A method for reducing the level of acrylamide in food, comprising:
   (1) adding a reducing sugar-altering enzyme to a food material, said sugar-altering enzyme comprising aldose reductase, wherein said food material comprises reducing sugar;
   (2) optionally mixing the enzyme with the food material;
   (3) allowing a sufficient time for the enzyme to react with the reducing sugar;
   (4) optionally deactivating or optionally removing the enzyme; and
   (5) heating the food material to form the finished food product.

4. The method of claim 3, wherein said method further comprises adding glucose oxidase, pyranose oxidase, aldose dehydrogenase, or a mixture thereof, to the food material.

5. The method of claim 3, wherein the level of acrylamide in the finished food product is reduced by at least about 10%.

6. The method of claim 5, wherein the level of acrylamide in the finished food product is reduced by at least about 30%.

7. The method of claim 6, wherein the level of acrylamide in the finished food product is reduced by at least about 50%.

8. The method of claim 7, wherein the level of acrylamide in the finished food product is reduced by at least about 70%.

9. The method of claim 8, wherein the level of acrylamide in the finished food product is reduced by at least about 90%.

* * * * *